United States Patent [19]
Lin et al.

[11] Patent Number: 5,993,475
[45] Date of Patent: Nov. 30, 1999

[54] TISSUE REPAIR DEVICE

[75] Inventors: Steve T. Lin; Steven L. Krebs, both of Fort Wayne, Ind.

[73] Assignee: Bristol-Myers Squibb Co., New York, N.Y.

[21] Appl. No.: 09/064,254

[22] Filed: Apr. 22, 1998

[51] Int. Cl.$^6$ .................................................. A61B 17/08
[52] U.S. Cl. ............................ 606/213; 606/76; 606/78; 606/216
[58] Field of Search .................................... 606/213, 215, 606/151, 157, 216, 72, 76, 78

[56] References Cited

U.S. PATENT DOCUMENTS

| | | | |
|---|---|---|---|
| 3,565,869 | 2/1971 | DeProspero | 260/78.3 |
| 3,636,956 | 1/1972 | Schneider | 128/335.5 |
| 4,884,572 | 12/1989 | Bays et al. | 128/334 |
| 4,895,148 | 1/1990 | Bays et al. | 606/213 |
| 4,898,186 | 2/1990 | Ikada et al. | 606/62 |
| 4,905,680 | 3/1990 | Tunc | 606/69 |
| 4,924,865 | 5/1990 | Bays et al. | 606/77 |
| 5,007,939 | 4/1991 | Delcommune et al. | 623/66 |
| 5,059,206 | 10/1991 | Winters | 606/213 |
| 5,084,050 | 1/1992 | Draenert | 606/77 |
| 5,129,906 | 7/1992 | Ross et al. | 606/77 |
| 5,154,189 | 10/1992 | Oberlander | 128/898 |
| 5,227,412 | 7/1993 | Hyon et al. | 523/105 |
| 5,234,006 | 8/1993 | Eaton et al. | 128/898 |
| 5,275,602 | 1/1994 | Shimizu et al. | 606/72 |
| 5,562,704 | 10/1996 | Tamminmäki et al. | 606/213 |
| 5,569,252 | 10/1996 | Justin et al. | 606/73 |
| 5,660,188 | 8/1997 | Groiso | 128/898 |

*Primary Examiner*—Michael Buiz
*Assistant Examiner*—Tina T. D. Pham
*Attorney, Agent, or Firm*—Cary R. Reeves

[57] ABSTRACT

A biodegradable device for repairing torn meniscal cartilage comprising a shaft and tissue gripping means at both ends. One end is adapted to pierce the tissue and the opposite end is adapted to fit a driver. The central portion of the device is essentially smooth along its length. The device has been subjected to a drawing operation after fabrication leaving the molecules in the shaft in a higher state of residual stress. When the device is exposed to an aqueous environment, the water absorbed by the polymer lowers the glass transition temperature of the polymer. Lowering glass transition temperature allows increased molecular mobility causing the device to contract. The contraction pulls the torn tissues into close apposition during healing. As the tissue heals, the tension is released by the polymer resorbing.

7 Claims, 2 Drawing Sheets

TISSUE REPAIR DEVICE

FIELD OF THE INVENTION

The present invention relates generally to the orthopedic surgical arts and more specifically to absorbable polymeric devices used to repair tissues, especially torn meniscal cartilage.

BACKGROUND OF THE INVENTION

Surgery to the human body often requires the attachment of tissues adjacent one another such as in the repair of the knee. The human knee joint contains a pair of cartilage pads which function to absorb shock and prevent friction between the opposing bones in the joint. Each pad is called a meniscus. The two pads are referred to as the meniscal cartilage. One or both of these pads can become torn causing pain and debilitation. If these tears are not treated, further deterioration of the joint can occur. Past medical treatment involved excision of the torn cartilage, sometimes including complete removal of the meniscus. Complete removal of the meniscus has been shown to cause degenerative changes in the joint, often resulting in a joint replacement. Modern surgical treatment focuses on repair of the tissue rather than excision. The most popular method of treatment involves the use of arthoscopic means to access the joint. The devices used to repair the cartilage range from sutures to staples and tacks such as taught in U.S Pat. No. 5,059,206. Requirements that are common to all of these devices are the need for the device to hold the torn tissue in close apposition and for the device to resorb after the tissues have healed. Regarding the first requirement, sutures can be tightened to hold the tissues close together when first applied but the tension is variable between each stitch and the sutures will loosen with time. Staples can be difficult to place and once placed there is no ability to adjust the compression between the opposing surfaces of the torn cartilage. Regarding the second requirement, resorbtion, or dissolution over time, of the device removes the need for later removal of the device and also removes the possibility of the device interfering with the normal functioning of the cartilage if the device was not removed.

SUMMARY OF THE INVENTION

The present invention solves the problems of the prior art by providing a tissue repair device composed of a drawn biodegradable polymer. The repair device makes use of molecular orientation, residual stress, and $T_g$ depression to provide a compressive force across torn tissue. The repair device of the present invention includes barbs or hooks at either end of the device to hold it firmly in the tissue while the force is applied.

DETAILED DESCRIPTION OF THE INVENTION

The following descriptions of the preferred embodiment are not intended to be exhaustive or to limit the invention to the precise forms disclosed rather they are chosen in order to explain the invention so that one skilled in the art might utilize their teachings.

Figure 1:
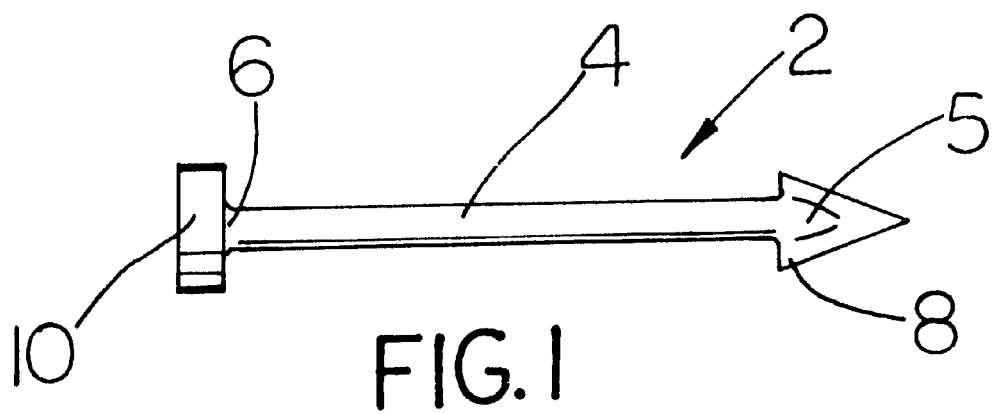
FIG. 1 is a side view of finished repair device according to the present invention.

FIG. 1 illustrates one embodiment of the invention. The device 2 comprises a longitudinally oriented bioresorbable polymer shaft 4, having two ends 5 and 6. The first end 5 of the shaft has a tapered point for penetrating tissue. Nearby the first end are a plurality of gripping means 8, such as barbs, for gripping tissue. The gripping means allow for movement in one direction. The second end 6 terminates in an end cap 10 for applying a compressive force to tissue and adapted for receiving a driver. The shaft 4 is smooth and separates the first and second ends 5 and 6.

Figure 2:
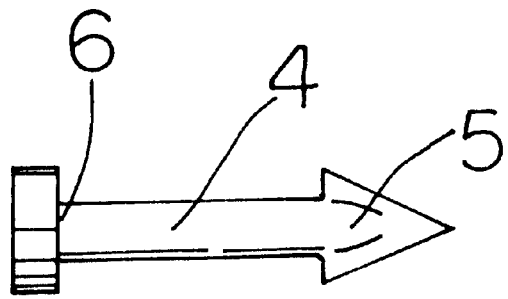
FIG. 2 is a side view of the repair device of FIG. 1 prior to the drawing operation.

The repair device is first molded of a bioresorbable material to form the as-molded device shown in FIG. 2. After molding the shaft 4 is drawn, or stretched, to align the polymer molecules. Drawing the polymer aligns the molecules and leaves the molecules in a state of residual stress. The diameter of the shaft 4 is reduced and it is lengthened after drawing.

Figure 3:
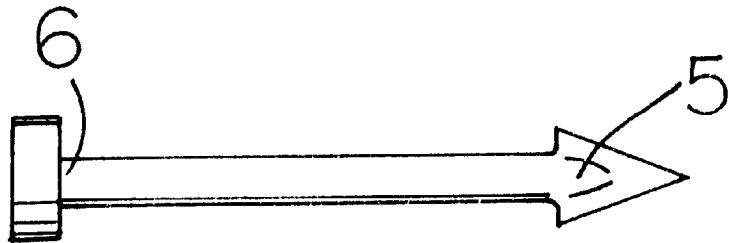
FIG. 3 is a side view of the repair device of FIG. 1 after exposure to an aqueous environment.

The residual stress in the device is a key component of the action of the device. When an absorbable polymer is placed in an aqueous environment the water acts as a solvent for the amorphous regions of the polymer, lowering the glass transition temperature of the polymer. The glass transition temperature is the temperature at which molecular motion increases to the point of allowing the polymer to become more flexible. Since the polymer molecules in the shaft 4 of the device are stretched and under stress prior to exposure to an aqueous environment they will shrink back to a percentage of their original length when exposed to water. This shrinkage pulls the first end 5 and second end 6 of the device towards one another as shown in FIG. 3. The end cap 10 holds the second end 6 in place relative to adjacent tissues. The barbs 8 on the first end 5 of the device hold the first end of the device relative to adjacent tissue. Since the first end 10 and second end 11 of the device are firmly fixed in the tissue adjacent each end, the shrinking central portion applies a compressive force that pushes the tissues together. As the tissue heals, the pressure on the tissue is released by the polymer resorbable.

Figure 4:
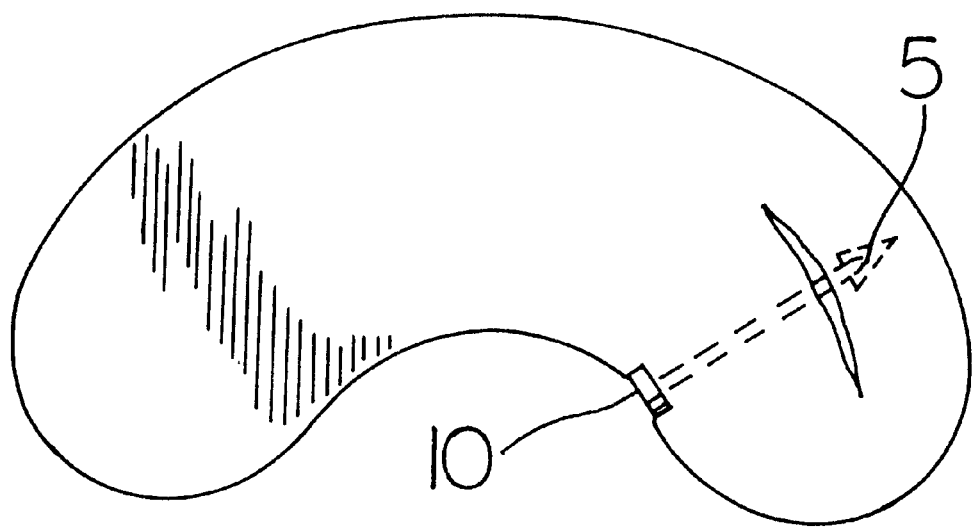
FIG. 4 is a top view of the repair device of FIG. 1 just after insertion into tissue and before exposure to water has caused contraction of the polymer.
Figure 5:
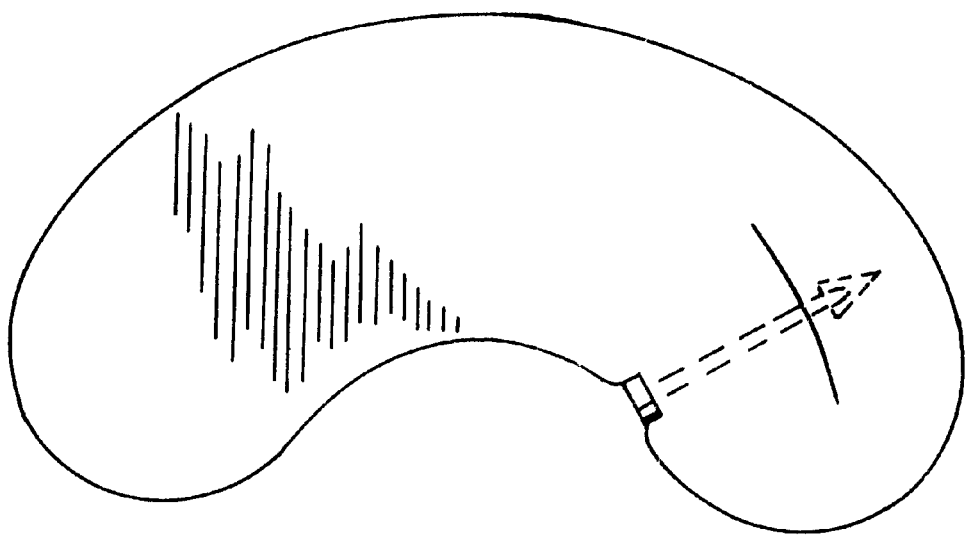
FIG. 5 is a top view of the repair device of FIG. 1 after insertion into tissue and after exposure to water has caused contraction of the device.

FIG. 4 illustrates the device as implanted in a meniscal cartilage. A driver is used to press against the end cap 10 so that the first end 5 of the device is inserted into the meniscal cartilage, penetrating the cartilage. The device is advanced through the cartilage passing across the tear and penetrating to the opposite side of the tear. Once the device is placed in the cartilage, the driver is removed. FIG. 5 illustrates the action of the device after sufficient exposure to water. The device will contract and draw the barbs 8 and end cap 10 toward one another thereby pulling the torn tissue surfaces together. It should be understood that the invention is not to be limited to the precise forms disclosed rather, they may be modified within the scope of the appended claims.

What is claimed is:

1. A tissue repair device comprising a shaft including a longitudinal axis and first and second ends spaced along the axis, each of the first and second ends including gripping means for gripping tissue, the shaft being responsive to exposure in an aqueous environment to shrink and compress tissue along the longitudinal aids.

2. The tissue repair device of claim 1 wherein the first end further includes a tapered tip for penetrating tissue.

3. The tissue repair device of claim 1 wherein the gripping means includes barbs extending from the shaft.

4. The tissue repair device of claim 1 wherein the second end is adapted to be driven by a driver.

5. The tissue repair device of claim 1 wherein the shaft includes a bioresorbable polymer having residual stresses imparted into it and preserved in it along the longitudinal axis, the resorbable polymer being responsive to exposure in an aqueous environment to shrink along the longitudinal axis.

6. The tissue repair device of claim 1 wherein the shaft comprises a drawn, oriented polymer.

7. The tissue repair device of claim 5 wherein the shaft is responsive to continued exposure in an aqueous environment to resorb and ease tissue compression.

* * * * *